United States Patent
Freund et al.

(10) Patent No.: US 6,748,792 B1
(45) Date of Patent: Jun. 15, 2004

(54) IMPAIRMENT DETECTION AND INTERLOCK SYSTEM WITH TESTER IDENTIFICATION

(75) Inventors: Richard C. Freund, Cincinnati, OH (US); Thomas E. Knowles, Batavia, OH (US); Sherman Couch, West Chester, OH (US)

(73) Assignee: LifeSafer Interlock, Inc., Cincinnati, OH (US)

( * ) Notice: Subject to any disclaimer, the term of this patent is extended or adjusted under 35 U.S.C. 154(b) by 0 days.

(21) Appl. No.: 10/384,109

(22) Filed: Mar. 7, 2003

(51) Int. Cl.[7] .................... G01N 33/497; B50K 28/06; B60R 25/10
(52) U.S. Cl. .................... 73/23.3; 422/84; 180/272; 340/426.1; 340/426.11; 340/426.19; 340/426.2; 340/426.21; 348/148; 600/532; 600/543
(58) Field of Search .................... 73/23.3; 422/84; 600/532, 543; 348/143, 148; 340/426.1, 426.11, 426.19, 426.2, 426.21, 427.71; 180/272; 431/90

(56) References Cited

U.S. PATENT DOCUMENTS

| | | | |
|---|---|---|---|
| 3,824,538 A | * | 7/1974 | Stemp .................... 180/272 |
| 4,665,385 A | * | 5/1987 | Henderson .................... 73/23.3 |
| 4,738,333 A | | 4/1988 | Collier et al. .................... 180/272 |
| 4,809,810 A | * | 3/1989 | Elfman et al. .................... 180/272 |
| 4,843,377 A | | 6/1989 | Fuller et al. .................... 340/573 |
| 4,901,058 A | | 2/1990 | Comeau et al. |
| 4,902,628 A | | 2/1990 | Blair |
| 4,912,458 A | | 3/1990 | Comeau et al. |
| 4,914,038 A | | 4/1990 | Jewitt |
| 4,916,435 A | * | 4/1990 | Fuller .................... 340/573.4 |
| 4,999,613 A | | 3/1991 | Williamson et al. .................... 340/573 |
| 5,734,090 A | | 3/1998 | Koppel et al. |
| 5,876,926 A | | 3/1999 | Beecham |
| 6,034,622 A | | 3/2000 | Levine |
| 6,104,809 A | | 8/2000 | Berson et al. |
| 6,149,440 A | | 11/2000 | Clark et al. |
| 6,198,996 B1 | | 3/2001 | Berstis |
| 6,229,908 B1 | | 5/2001 | Edmonds, III et al. |
| 6,608,399 B2 | * | 8/2003 | McConnell et al. .................... 307/10.1 |
| 2002/0084130 A1 | * | 7/2002 | Der Ghazarian et al. ... 180/272 |
| 2003/0117287 A1 | * | 6/2003 | Crespo .................... 340/576 |

OTHER PUBLICATIONS

Douglas J. Belmess, *Best Practices for Alcohol Interlock Programs*, Traffic Injury Research Foundation, Apr. 2001.

U.S. patent application entitled Substance Testing Devices with Photo Identification, dated Dec. 21, 2001.

Keliann M. Argy, *Historical Synposis*, Children and Adult Road Safety Systems, Inc., 1999.

Felix J. E. Comeau, *Ignition Interlock Devices Support Program Development*, Alcohol Counter Measure Systems Corp.

* cited by examiner

*Primary Examiner*—Daniel S. Larkin
(74) *Attorney, Agent, or Firm*—Wood, Herron & Evans, L.L.P.

(57) ABSTRACT

A system, device, and method for determining whether an individual has consumed, is intoxicated, or is otherwise impaired by alcohol is disclosed. Further, a device capable of positively identifying the person who provides the impairment test is disclosed. The impairment detection and interlock system disclosed accomplishes this with the use of a video camera that selectively saves images, and an attitude evaluator and, in some embodiments, an exposure evaluator, which ensures that the video camera captures the identity of the tester. A device holster may also be used to facilitate video surveillance.

30 Claims, 5 Drawing Sheets

IMPAIRMENT DETECTION AND INTERLOCK SYSTEM WITH TESTER IDENTIFICATION

FIELD OF THE INVENTION

The present invention relates to devices commonly referred to as "sobriety interlocks," which are connectable to a vehicle, such as a car or a truck, and which normally operate to disable the vehicle from starting if it is determined, through the delivery of a breath alcohol test, that the intended user has recently consumed alcohol. More particularly, the present invention relates to an alcohol interlock device which is able to positively identify the tester who provides an impairment sample before the vehicle is allowed to start, as well as the tester who provides subsequent samples while operating the vehicle. The invention also relates to identifying testers who must provide samples for alcohol abstinence monitoring.

BACKGROUND OF THE INVENTION

The operation of motor vehicles by individuals who are impaired or under the influence of alcohol is a major safety problem. In addition, the operation of a vehicle while under the influence of alcohol can not only put the operator in severe danger, but can also affect the safety of others, such as the drivers and passengers in other vehicles.

Recognizing the seriousness of driving while under the influence, many laws have been written prohibiting such conduct and providing various methods for dealing with such offenses when they occur. For example, a court or licensing authority may suspend the driving privileges of someone who is convicted of driving while under the influence of alcohol or may require that a sobriety interlock system be installed in his or her vehicle. Additionally, a state may require repeat offenders to install such devises as a condition of having their license reinstated. Finally, abstinence from the use of any alcohol may be a condition of a repeat offender's parole or probation.

A sobriety interlock device, when installed in an individual's vehicle, requires that the individual pass a sobriety test before the vehicle can be started. However, since the use of impairment detection interlocks is normally done outside the presence of law enforcement or any other supervising authority, and since a penalty may be attributed to a failed test, e.g., the vehicle will not start and a condition of parole may be violated, there can be a temptation to tamper with the impairment detectors to attempt to fraudulently affect its results. For example, a sobriety interlock that uses a breath sample to determine intoxication could be defeated if someone who is not intoxicated, like a child, provides the sample. Once the clean sample is provided, and the vehicle starts, the impaired driver then drives away. If the designated tester has been drinking, he or she may ask someone who is sober to take the test for them and thus circumvent the interlock. Accordingly, there is a need to identify who is taking the test, whether the tester passed or failed, to minimize circumvention and to be able to impose violation sanctions.

Additionally, when a term of probation or parole requires alcohol abstinence or prohibits a person from attempting to operate a vehicle after consuming alcohol or after being impaired by alcohol, failing a breath test can result in incarceration. However, with past systems, when a test detected prohibited levels of alcohol, the intended tester, e.g., the owner of the vehicle, could simply argue that someone else took and failed the test and thus avoid incarceration.

To deter fraudulent testing or circumvention some systems require random retesting while the vehicle is in operation. However, just as a sober individual, like a child, can fraudulently take the initial test before the vehicle is allowed to start, that same individual could also ride along with the driver and fraudulently take a driving retest. Additionally, some systems require a user to perform a certain identifying act, such as a sequence of blows. However, breath pulse codes can be copied by others and, therefore, do not provide definite proof of the identity of the impairment tester.

Impairment detection systems are also used in conjunction with home confinement, or during an individual's probation. For example, as a term of probation, or as a term of a home confinement sentence, an individual may be required to periodically take a test for alcohol. Accordingly, a similar situation develops in that the identity of the user providing the sample must be confirmed. In an attempt to monitor and provide positive identification of the individual providing the sample, video cameras have been used. However, such monitoring can be less than desirable due to the amount of storage required by a video stream, the bandwidth required for transmission of such a video stream, and the requirement for a human monitor to review the video stream. The in home systems used for alcohol abstinence are typically not designed to be portable and generally cost more to operate than vehicle interlock systems. Moreover, the use of a camera in an automobile, or in a home, can further be defeated due to adverse lighting conditions or poor camera angles.

Accordingly, there is a need for a detection device to positively identify the individual who is subject to an impairment analysis. There is also a need for an impairment detection device that can desirably archive the requisite data to positively identify the impairment tester. There is also a need to deter circumvention of impairment detection systems. There is also a need to provide a low cost system for abstinence monitoring systems.

OBJECTS OF THE INVENTION

It is an object of the applicant's invention to improve the identification of the user of an impairment detection device. It is also an object of the applicant's invention to deter easy circumvention of an interlock system. It is another object of the applicant's invention to provide an improved impairment detection device for use in probation or home confinement situations.

SUMMARY OF THE INVENTION

The present invention achieves these objects and overcomes the foregoing and other shortcomings and drawbacks of interlock systems and methods heretofore known. The present invention comprises a camera built into the handheld alcohol sampling portion of an interlock device, which records the image of an individual as he is providing a breath sample.

The present invention utilizes a video camera to receive the image of the individual who is the subject of an impairment test and analysis. Moreover, in an effort to minimize fraudulent test activity, the present invention can further provide an exposure evaluator or monitor to evaluate whether the video images are properly exposed. The present invention further provides an attitude evaluator to ensure that the device is property positioned before, during, and after a test to ensure an acceptable identifying camera angle. The present invention can also utilize a holster whereby the camera can be required to be positioned so as to enable surveillance of the driver. Finally, the device provides for a timing module and calculator whereby only certain images corresponding to critical times during a test need to be saved.

The above and other objects and advantages of the present invention shall be made apparent from the accompanying drawings and the descriptions thereof.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

DETAILED DESCRIPTION OF THE INVENTION

Figure 1:
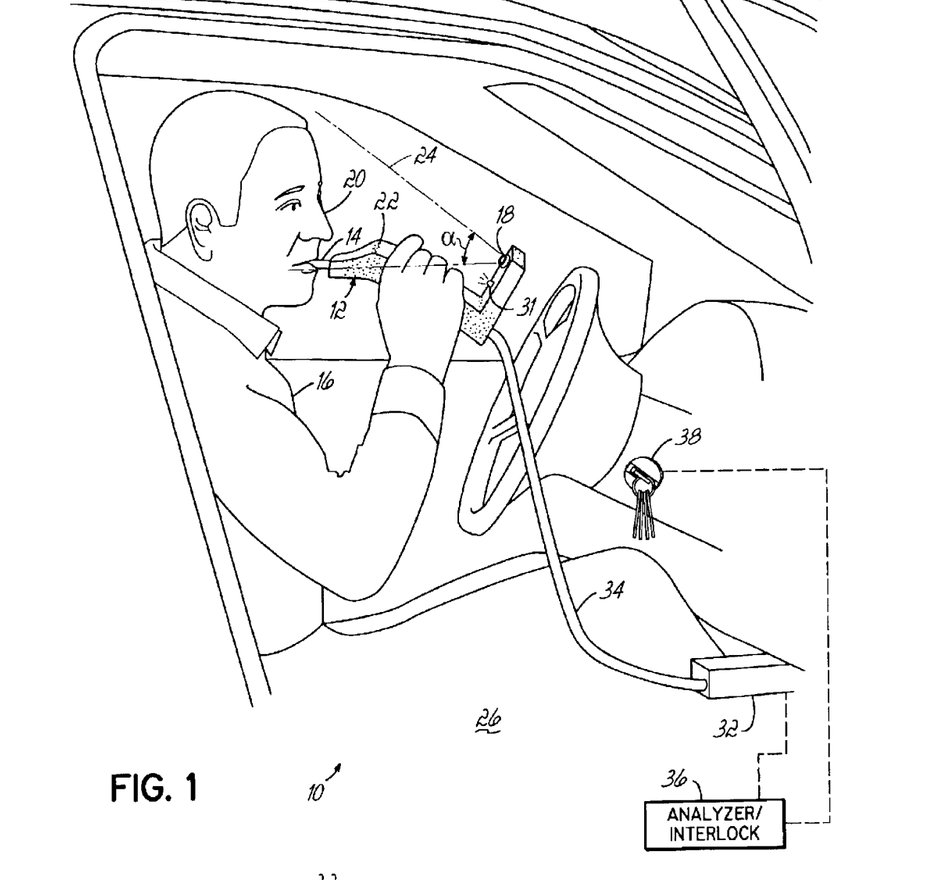
FIG. 1 is a perspective view of an embodiment of an impairment detection and interlock system with user identification according to the present invention.

As shown in FIG. 1, the system 10 includes a hand-held device 12 adapted for sampling a user's breath through a mouthpiece 14 through which a user 16 provides a breath sample. The mouthpiece 14 may be disposable and can be configured so as to be required to be locked in the device 12 before a test can be taken. The mouthpiece 14 may also be constructed of a material, such as hard plastic, that will be resistant to bending.

To determine a user's 16 blood-alcohol content (BAC) from his or her breath, breath-sampling devices 12 typically require a "deep-lung" breath sample. Hence, the air that must be blown into the mouthpiece 14 generally must comprise alveolar air, which occurs when an expiratory breath substantially exhausts the lungs. Since, breath expired from upper portions of the respiratory tract does not necessarily have an alcohol level proportional to that of the bloodstream, the breath-sampling or breath testing device 12 is adapted so as to prevent the processing of shallow exhalations, e.g., when a user 16 blows only short puffs of air expelled from the upper portions of his or her respiratory tract. One embodiment of the present invention ensures that a proper air sample will be given by including a pressure sensor in the device 12, which can determine when a deep-lung breath has been given. Typically, a user 16 is required to blow and hum for about five seconds.

The device 12 includes a video camera 18 positioned and adapted so as to have a camera angle α, which captures the identifying facial features 20 of a user 16 during an impairment test. In addition, the camera 18 further captures at least a portion 22 of the hand-held sampling device 12 and/or mouthpiece 14 to positively link the impairment sample tested and analyzed with the impairment tester 16. The field of view 24 of the camera 18 will also be such as to sufficiently record the location of the user 16 during the impairment test, e.g., whether he or she is sitting in the driver's seat 26, the passenger seat, or is outside of the vehicle 28.

Figure 1A:
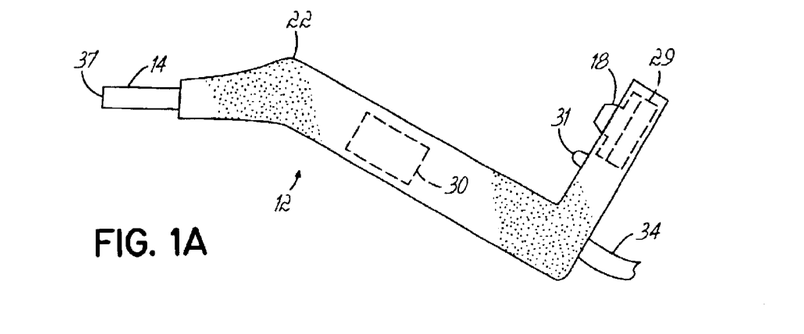
FIG. 1A is a perspective view of the impairment detection device with tester identification, as shown in FIG. 1.

In the embodiment of the present invention shown in FIG. 1A, an exposure monitor 29 is operatively connected to the camera 18, and can evaluate whether any video images are overexposed, e.g., a flashlight is shined in the camera lens, or underexposed, e.g., a thumb or other covering is placed over the lens, such that an identifiable image of a human face 20 is not captured by the camera 18.

The device 12 also contains an attitude evaluator 30, or attitude switch, which may utilize a standard mercury or roll ball switch known in the industry, which ensures that the unit 12 is properly orientated and positioned before, during, and after an impairment test. Specifically, the unit 12 is designed not to function if a user 16 were to invert the unit, or otherwise twist or turn it, such that the camera 18 would no longer be positioned to capture a user's face 20. Thus, a user 16 cannot take and pass a test which would allow the vehicle to start if the unit 12 is not properly positioned so as to capture an image of the user's face. Additionally, if the unit 12 was not properly positioned during a driving retest, violation sanctions, such as sounding the horn 25 or flashing lights 27, could be imposed.

The interlock system 10 further contains an indicator 31 whereby a user 16 is prompted to begin a test. As shown, the indicator 31 could reside on the hand-held device 12 and consist of a light, such as a light-emitting diode (LED), which could begin flashing to indicate a test is required. The LED could also provide feedback to a user, such as glowing solid, to indicate that the proper air sampling pressure is being applied to the mouthpiece 14.

Other forms of prompting and feedback could also be adapted as part of the present invention. For example, the indicator 31 could be a solid or flashing multicolored LED, or could consist of multiple LEDs, either of which could prompt a tester 16 to begin an impairment test. Such an indicator 31 can also inform a tester 16 that a proper sample has been given, can inform the tester 16 that the analysis sequence is underway, and can provide the impairment test results to the tester 16. It should also be appreciated that other indicators to prompt a user 16 to commence a test and/or provide feedback of that test could be used. For example, in a situation where a vehicle impairment detection and interlock system 10 is also being used to monitor an individual 16 during his or her term of probation, parole, or limited or full home confinement, the system 10 could be programmed to prompt a user 16 for a sample at random or at specific times throughout the day by sounding the vehicle's 28 horn 25. In addition to a horn 25, a test prompter could also be a regular or cellular telephone or pager (not shown). In sum, a user 16 could be prompted to begin an impairment test with an audio or visual indicator.

System 10 can be programmed to turn-on at specific times during the day in preparation for a test. For example, if a tester 16 always starts his or her car 28 at the same time of day, such a leaving for work or returning home from work, the system 10 can be programmed to begin warming up for the test a few minutes before these routine times. Similarly, if a tester 16 is required to take tests at set times throughout the day, the system 10 can be programmed to be ready at those times. This "instant on" capability reduces the total test time and eliminates any unnecessary warm-up delay, which typically increases in colder weather.

As illustrated in FIG. 1, the sampling device 12 of the interlock system 10 would typically be attached to a processor 32 via a flexible cord 34. The processor 32 will analyze a sample provided by an individual and determine whether an impairment condition exists. If the analyzer/interlock function 36 of the processor 32 determines an impairment condition exists, the vehicle's 28 ignition 38 will remain disabled. However, if the analyzer/interlock 36 determines no impairment exists, the ignition 38 of the vehicle 28 will be enabled and allow a driver 16 to start the engine.

The processor 32 will typically contain a data memory whereby the video images captured by the camera 18 and data corresponding to the date and time of the impairment test will be recorded. Such data can later be retrieved for analysis by a monitoring service via a cable, disk, memory card, or wireless connection, e.g., infra-red (IR), radio frequency (RF), or the like, and can be forwarded to law enforcement, employers, or the court system for appropriate actions. While such memory may be located in the processor box 32, it should be appreciated that such a memory module could equally be contained in the hand-held unit 12.

Figures 2, 2A:
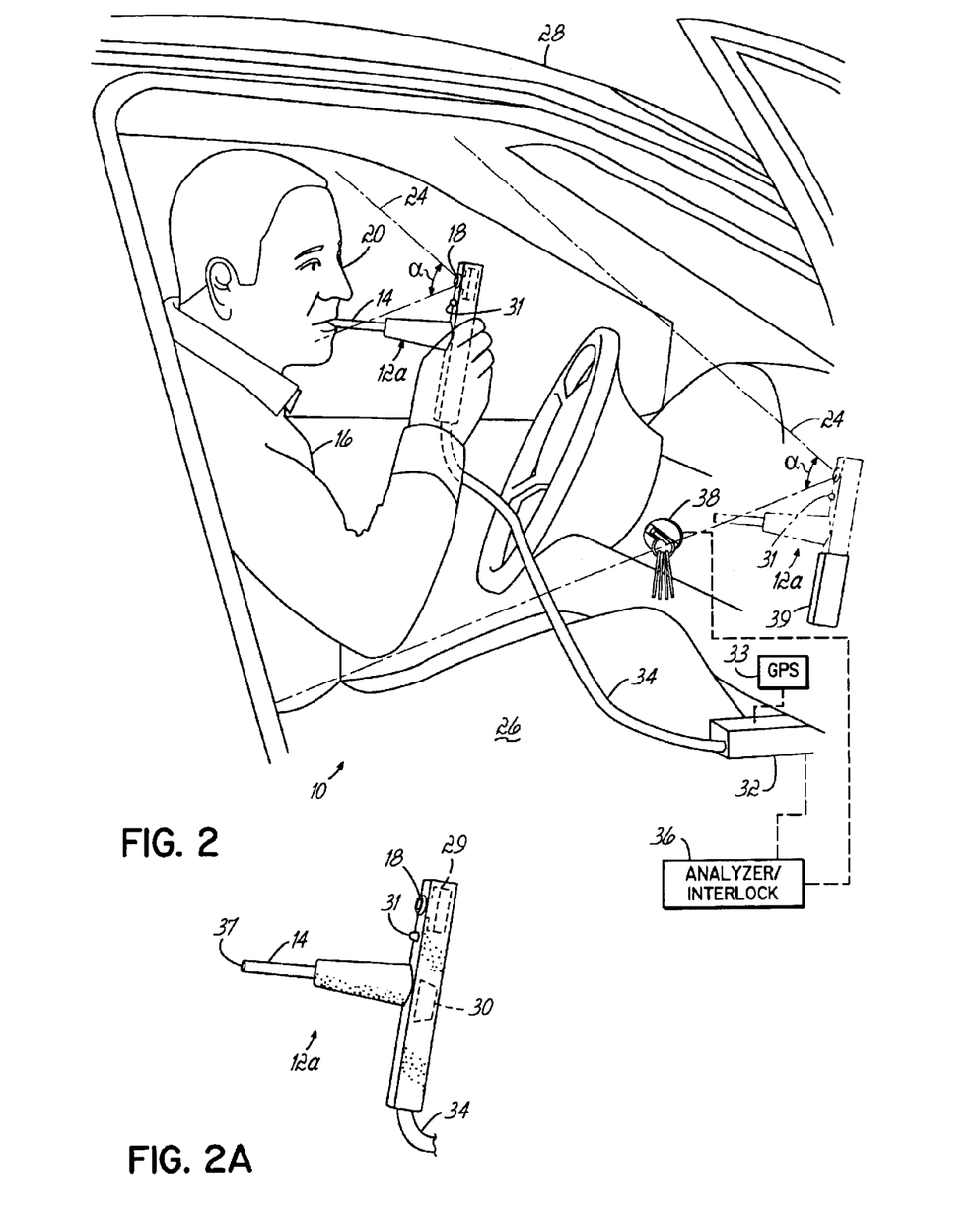
FIG. 2 is a perspective view of an alternative embodiment of an impairment detection and interlock system with user identification according to the present invention.
FIG. 2A is a perspective view of the impairment detection device with tester identification, as shown in FIG. 2.

FIGS. 2 and 2A show alternative embodiments of the system 10. Many of the components shown in FIGS. 2 and 2A are like the components of the embodiments shown in FIGS. 1 and 1A and, as such, are identified with the same numbers.

As shown, the handheld device 12a is properly gripped below the camera lens 18, allowing for an increased unobstructed view of a tester's 16 face. In this embodiment, the camera lens 18 will typically be set back about 10.16 cm (4") to 15.24 cm (6") from the tip 37 of the mouthpiece, so as to allow the field of view 24 to capture the face of the tester 16. Additionally, as shown, a holster 39 for the device 12a is mounted in the vehicle 28, e.g., on the dash. When the device 12a is holstered, the field of view 24 of the camera 18 will capture a broad, panoramic view of the driver's seat 26 area. The holster 39 can also contain a standard electronic or magnetic connection or switch, or other like contact sensor (not shown), which is well known in the industry, whereby a determination can be made whether and when the device 12a is holstered.

Additional components, known in the industry, can be added to the system 10 to provide for added capabilities. For example, a global positioning system (GPS) 33 can be incorporated into the system 10, whereby the exact location of the vehicle 28 when a violation occurred could be recorded. Such a capability may provide corroborating evidence of the tester's 16 identity, e.g., if the location happens to be in the tester's 16 garage 41, or may provide useful geographical information for legal jurisdictional purposes. Additionally, a system 10 that also has wireless communication transmitter, e.g., a radio function, could be effective in notifying the monitoring facility or law enforcement of a failed impairment test. If the system 10 also had a GPS capability, law enforcement could be dispatched to the location of the vehicle 28 when there was a failed test. This capability could be extremely beneficial to intercept someone who is driving while impaired. Additionally, a system 10 with a wireless communication transceiver, e.g., cellular telephone, enabling two way communication, could also be used by the monitoring facility to dynamically order a recall of the system 10 or lock the ignition, in response to a violation. Finally, a system 10 with a wireless communication receiver could be used by a monitoring facility to dynamically request random alcohol tests.

Figure 3:
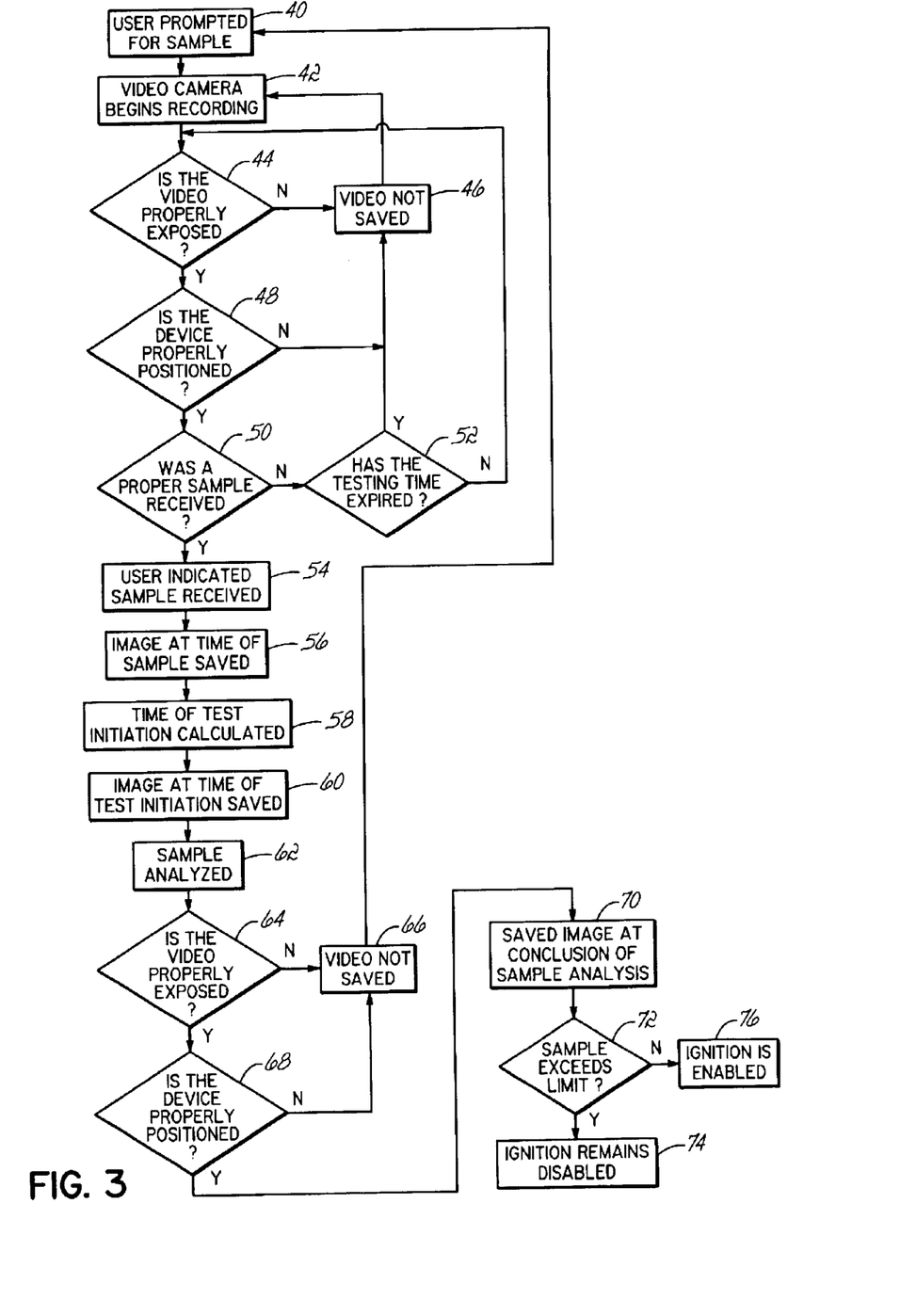
FIG. 3 is a flow chart of the process performed by an embodiment of the present invention.

The flow chart shown in FIG. 3 depicts the representative processing performed by an embodiment of the impairment detection and interlock system 10. The process begins with a tester 16 being prompted (Block 40) to take an impairment test, e.g., provide a sample of alveolar gas. Typically, this prompting will occur when the tester 16 attempts to start the vehicle 28 by turning the ignition switch 38. This prompting may be from a flashing LED 31, an audio prompt, or the like. Additionally, if the system 10 unitizes a holster 39, the tester 16 may be prompted to ensure that the device 12a is properly placed in the holster 39 prior to beginning the testing sequence.

When the tester 16 is prompted for a sample (Block 40), the video camera 18 begins recording (Block 42). In an embodiment of the present invention with an exposure evaluator 29, as the video camera 18 is recording, the video exposure evaluator 29 determines whether the video images are properly exposed (Block 44). If the video images are not properly exposed, which may occur if the tester 16 attempts to tamper with the impairment test by shining a flashlight in the camera lens to overexpose an image or somehow blocking the camera lens to underexpose the image, the video images generally are not saved (Block 46), and the impairment test must begin again (Block 42). Alternatively, while not shown in FIG. 3, the non-image, i.e., that which is over or underexposed, could be saved as evidence of tampering with the system 10, which is typically a violation of a condition of probation or use of the system 10.

If the video images are properly exposed (Block 44), or in an embodiment without an exposure evaluator 29, the attitude evaluator 30 next determines whether the device 12 is properly orientated and positioned (Block 48). Here again, if the device 12 is not properly positioned, no video images are saved (Block 46), and the video camera 18 begins recording anew (Block 42). However, if the device 12 is properly positioned and orientated (Block 48), a determination is next made whether a proper sample, suitable for analysis, was received (Block 50). If a proper sample was not received (Block 50), a determination is made whether the allotted time for testing has expired (Block 52). If the allotted time for testing has not expired (Block 52), the evaluation sequence, beginning with the evaluation of whether the video images are properly exposed (Block 44), begins again. If the allotted time for testing has expired (Block 52), no video images are saved (Block 46), and the process begins again (Block 42). In other words, an individual's 16 dilatory conduct would not defeat the impairment detection and interlock system 10 by using up all of the video image storage memory before an impairment sample was provided.

If a proper sample sufficient for impairment analysis was received (Block 50), the user 16 is provided an indication that a proper sample was received and recorded. (Block 54). Also, an image from the recorded video stream corresponding to the time the sample was received will be saved (Block 56). In other words, according to the principles of the present invention, only specific photos or images corresponding to specific times of key events during the impairment testing sequence need to be saved. Thus the need for the capability and memory for archiving large video clips is unnecessary.

In addition to saving a video image from the time at which the individual 16 provided a proper sample (Block 50), the system 10 will also calculate the time at which an earlier photo will be archived, corresponding to the time the impairment test was initiated (Block 58). In other words, in a breath-sampling device 12, a pressure sensor determines when a proper sample has been provided and a timer/calculator determines the earlier time at which an image corresponding to the initiation of the test should be saved. Once this determination is made, an image corresponding to the initiation of the impairment test is also saved (Block 60). Moreover, any temporarily saved video streams prior to the time that a valid sample was received could, at this point, be deleted or overwritten by a video stream recording the events occurring while the sample is being analyzed (Block 62). Nevertheless, in an embodiment of the present invention with an exposure evaluator 29, another determination is made whether the video camera 18 is continuing to receive properly exposed images (Block 64). If the images recorded by the video camera 18 are not properly exposed (Block 64), no video images are saved (Block 66), and the user 16 is again prompted for a sample (Block 40). If the video images are properly exposed (Block 64), or in an embodiment of the present invention without an exposure evaluator 29, another determination is next made whether the device 12 is still properly orientated and positioned (Block 68). If the device 12 is no longer properly orientated or positioned (Block 68), no video images are saved (Block 66), and the user 16 is prompted to begin the impairment test again (Block 44). If, however, the device 12 remains properly orientated and positioned (Block 68), then an image will also be saved at the conclusion of the impairment analysis (Block 70). It should be appreciated, that in an embodiment of the system 10 utilizing a holster 39, the determination of whether the device 12a is properly positioned after the test may be determined by whether the device 12a has been placed back in its holster 39.

If the impairment analysis determines that an individual's 16 BAC exceeds a predetermined limit (Block 72), the ignition 38 of the vehicle 28 remains disabled (Block 74). However, if the impairment sample is below the limit (Block 72), the ignition 38 is enabled (Block 76), and the user 16 is permitted to start and operate the motor vehicle 28.

In addition, while only the archiving of a sequence of three images for a particular impairment test has been shown, in alternative embodiments, any number of images could be saved. However, the saving, with a time and date stamp, of the photo of the individual 16 who initiated the test, blew the test if a breath-sampling device was employed, and the individual 16 who was in possession of the device 12 when the sample was processed and analyzed should be sufficient for law enforcement or other supervisory purposes. Moreover, as discussed, the presence of the device 12 or mouthpiece 14 in each photo will link the photos to the impairment test result and the corresponding identity of the tester 16. Additionally, in a system 10 with a holster 39, the panoramic surveillance images recorded when the device 12a is in the holster 39 at the beginning and at the end of the test may also be saved. Finally, the results of the test, i.e., the tester's 16 blood alcohol, and whether the tester 16 passed or failed the test, is also saved.

Once the vehicle 28 is started, in a system 10 utilizing a holster 39, the driver 16 will typically be alerted if the device 12a is removed from the holster 39. This warning may be an audio or visual indicator and will typically be of an escalating nature. In other words, should the device 12a be accidentally or inadvertently dislodged from the holster 39, an adequate notice to the driver 16 will be provided to allow him or her to promptly replace the device 12a in the holster 39. However, if the device 12a is not promptly holstered, or if it is repeatedly removed from the holster 39, the system 10 may record a tamper violation and begin sounding the horn 25 and flashing the vehicle's 28 lights 27.

Figure 4:
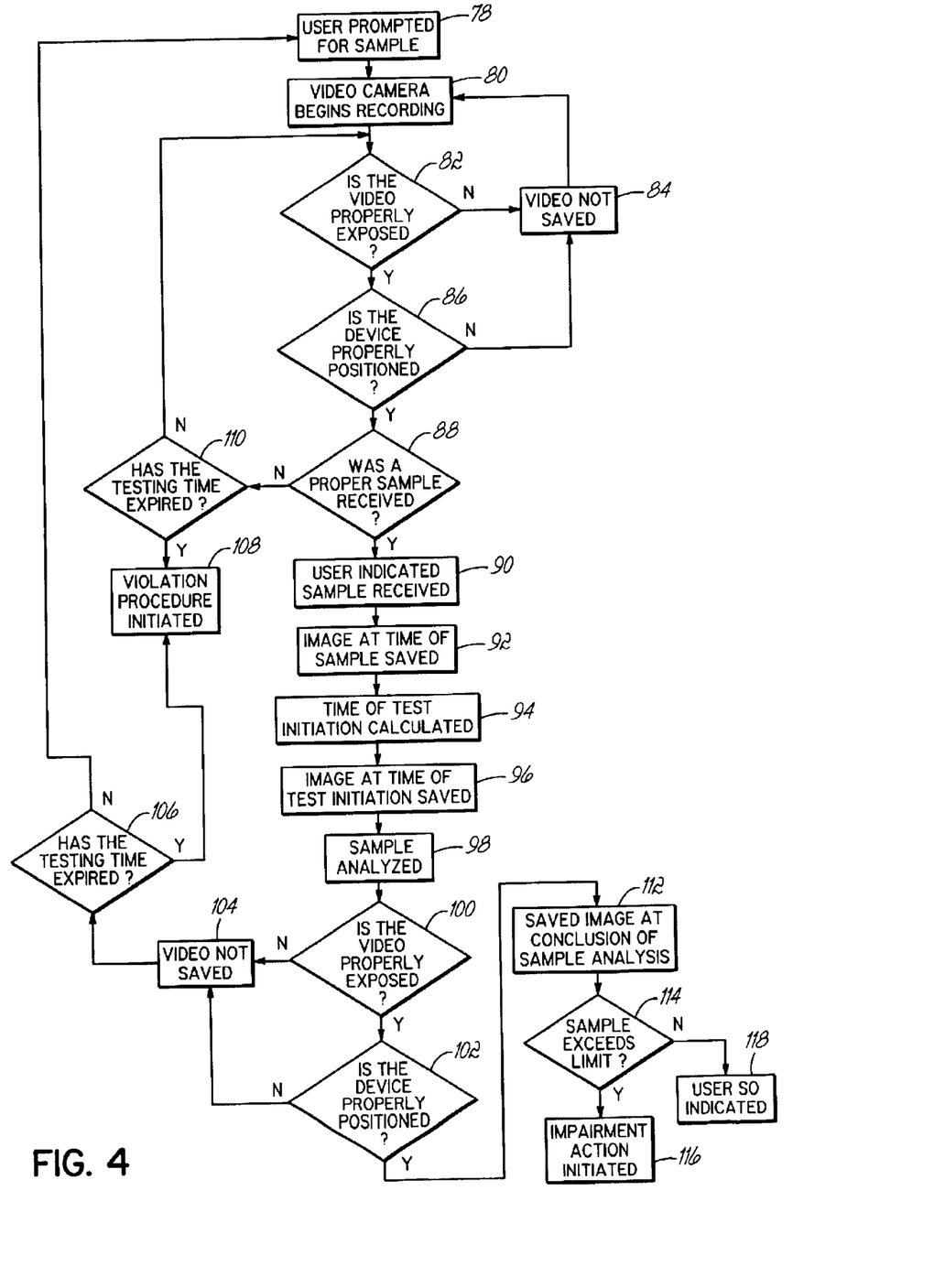
FIG. 4 is a flow chart of the process performed by another embodiment of the present invention.
Figure 5:
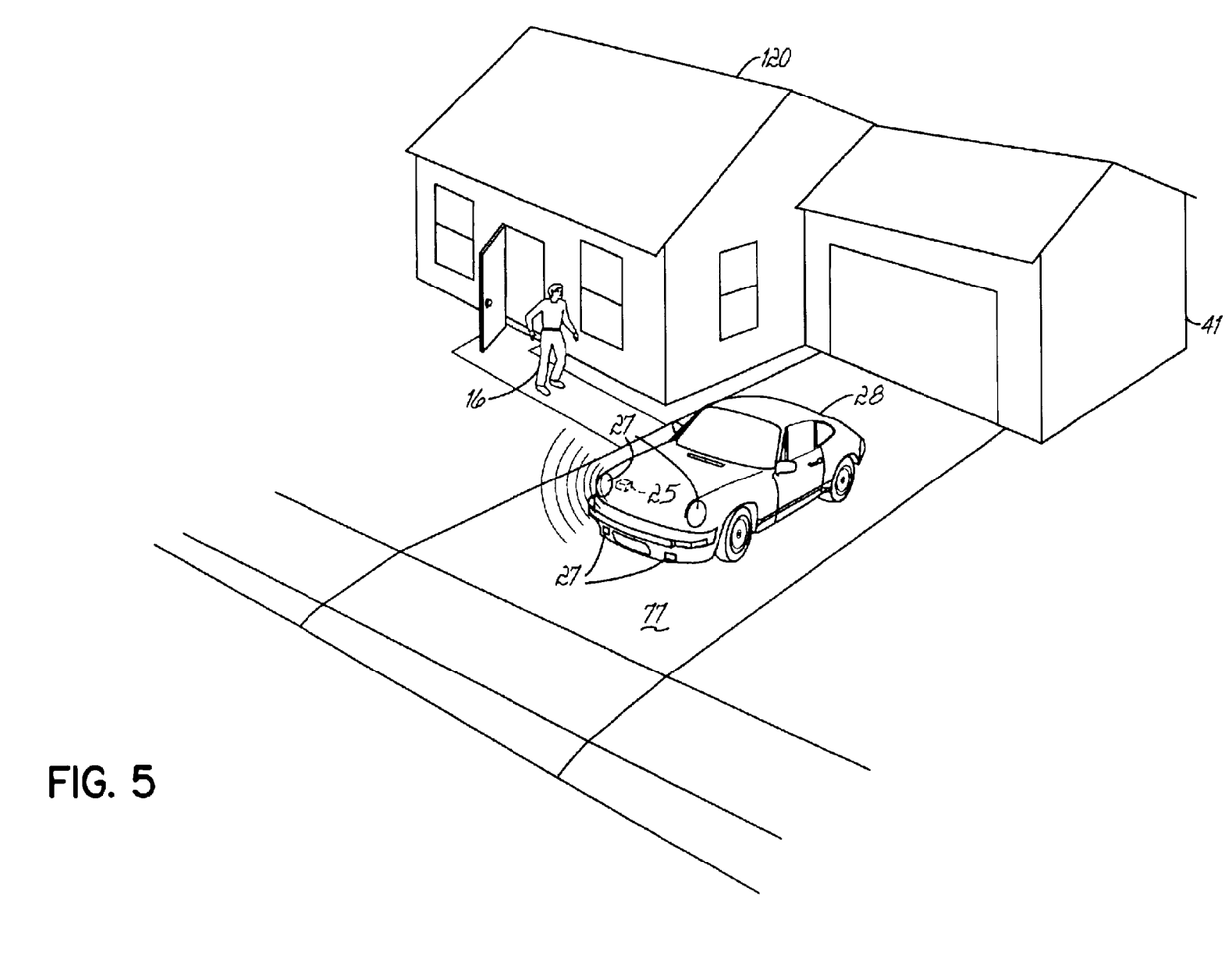
FIG. 5 is a perspective view of showing the use of the present invention shown in FIGS. 1, 1A, 2, and 2A in the context of a home driveway test.

The flow chart shown in FIG. 4 depicts the representative processing performed by the impairment detection and interlock system 10 in a situation where an impairment test is conducted while the vehicle 28 is being operated, i.e., started and/or being driven, or an impairment test is requested of an individual 16 who is under a home confinement sentence, i.e., a driveway 77 test, such as shown in FIG. 5. For a driving test, as before, the user 16 is prompted (Block 78) to begin an impairment test. This prompting may be from a flashing LED 31, or, in the context of a driveway 77 test, may be the sounding of a vehicle's 28 horn 25. A tester 16 may also be prompted to take a driveway 77 test by a telephone call or page from a monitoring facility. Alternatively, a tester 16 may be notified that driveway 77 tests will be required at certain time intervals or certain times, such as "high risk" times for alcohol detection, like early in the morning.

When the tester 16 is prompted (Block 78), the video camera 18 begins recording a temporary stream of video images (Block 80). As before, in an embodiment of the present invention with an exposure evaluator 29, the exposure evaluator 29 determines whether the video images are properly exposed (Block 82). If the video images are not properly exposed, the video stream is not saved (Block 84), and the camera 18 begins temporarily saving a new video stream (Block 80). Alternatively, while not shown in FIG. 4, the non-image, i.e., that which is over or underexposed, could be saved as evidence of tampering with the system 10, which is typically a violation of a condition of probation or use of the system 10.

If the images are being properly exposed (Block 82), or in an embodiment without an exposure evaluator 29, a determination is made whether the device 12 is properly positioned and orientated (Block 86). If the device 12 is not properly orientated (Block 86), no video images are saved (Block 84), and the process begins again (Block 80). However, if the device 12 is properly orientated (Block 86), and if a proper sample suitable for analysis was received (Block 88), the user 16 is so informed (Block 90) through, for example, an LED 31. As before, an image from the video stream corresponding to the time the sample was actually provided, as indicated by a pressure sensor in a breath test, is saved (Block 92). A prior image corresponding to the time the test was initiated is also calculated (Block 94) and saved (Block 96). While the sample is being analyzed (Block 98), in an embodiment with an exposure evaluator 29, another determination is made whether the video images are still being properly exposed (Block 100). In addition, while the sample is being analyzed (Block 98), another determination is made whether the device 12 is still properly orientated and positioned (Block 102). In an embodiment of the system 10 utilizing a holster 39, the determination of whether the device 12a is properly positioned after the test may be determined by whether the device 12a has been placed back in its holster 39. If the images are not properly exposed or the device 12 is not properly positioned, the video images are not saved (Block 104) and, if the time for testing has not expired (Block 106), the user 16 is again prompted to begin the test (Block 78). If, however, the time for testing has expired (Block 106), the impairment detection and interlock system 10 initiates a violation procedure (Block 108). A violation procedure (Block 108) will also be initiated if the time for testing has expired (Block 110) prior to a user 16 giving a proper sample (Block 88). If the time for testing has not expired (Block 110), the evaluation sequence, beginning with the evaluation of whether the video images are properly exposed (Block 82), begin again. However, if a driver 16 is operating a vehicle 28 and is prompted (Block 78) to provide a sample and ignores that prompt, after a certain predetermined amount of time (Block 110) a violation procedure will be initiated (Block 108). Likewise, if the impairment detection and interlock system 10 wakes up and prompts a user 16 at home to give an impairment sample (Block 78) and the individual 16 ignores the request for a test, after a period of time (110), a violation procedure will also be initiated (Block 108).

In a driving context, the violation procedure (Block 108) could consist of sounding the horn 25 and/or flashing the lights 27. Similar attention-getting devices could be employed in the driveway 77 context, where a user 16 may initially be prompted for a sample (Block 78) by the impairment detection and interlock system 10 sounding the vehicle's 28 horn 25, which may also continue to honk if the user 16 ignores the request for a test.

In an embodiment of the present invention with an exposure evaluator 29, if the video images are properly exposed (Block 100), and if, in all embodiments, the device 12 remains properly positioned (Block 102) while the sample is being analyzed (Block 98), then an image is saved at the conclusion of the analysis process (Block 112). If the impairment sample exceeds the limits for alcohol (Block 114), the appropriate impairment action begins (Block 116). In a driving test, this may consist of sounding the horn 25 or flashing the vehicle's 28 lights 27 to attract attention. In the context of a driveway 77 test, the failed impairment test is recorded and can be accessed for the appropriate disciplinary action. However, if the impairment limit has not been exceeded (Block 114), the user 16 receives an appropriate indication (Block 118) and, in the context of a driving test, may continue operating the vehicle 28 as normal, or, in the context of a driveway 77 probation test, may simply return to his or her house 120.

It should be appreciated that in addition to the sanction of the vehicle 28 not starting or the flashing the lights 27 and sounding the horn 25 the system 10 may also order an early recall for as a result of a violation. In other words, a user 16 may be alerted that her or she must return the system 10 to the monitoring facility within a certain time period, or the system 10 may go into lock-out mode, requiring the monitoring facility to "unlock" the vehicle. If the user 16 waits until the system 10 goes into lock-out mode, the vehicle 28 may have to be towed to the monitoring facility.

FIG. 5. Further illustrates the use of the present invention for a driveway 77 test. The ability to use the same impairment detection system 10 as both an interlock as well as in alcohol abstinence monitoring can have significant cost savings. Such abstinence tests could be at random or set times during the day. In either case, the system 10 could be programmed to warm-up prior to the test to minimize the testing time. Additionally, the system can record that a required test was not taken, if such happens to be the case. Finally, another advantage of using interlock system 10 for abstinence testing is that a tester 16, need not necessarily be confined to his or her house 120, but rather need only to be near their vehicle 28.

While the present invention has been illustrated by description of various embodiments and while these embodiments have been described in considerable detail, it is not the intention of the applicant to restrict or in any way limit the scope of the claims to such detail. Additional advantages and modifications will readily appear to those skilled in the art. The invention in its broader aspect is, therefore, not limited to the specific details, representative apparatus and method, and illustrative example shown and described. Accordingly, departures may be made from such details without departing from the spirit or scope of the applicant's general inventive concept.

This has been a description of the present invention, along with the preferred method of practicing the invention currently known to the inventor. However, the invention itself should be defined only by the claims.

We claim:

1. An apparatus for positively identifying the user of an alcohol impairment detection system comprising:
    a hand-held sampling device having a handpiece adapted to receive a sample; and
    a video camera integral with said handpiece.

2. The apparatus of claim 1 wherein the hand-held sampling device is a breath testing device.

3. The apparatus of claim 1 further comprising an image exposure evaluator operatively connected to the video camera.

4. The apparatus of claim 1 further comprising a hand-held sampling device attitude evaluator integral with the hand-held sampling device.

5. The apparatus of claim 1 further comprising a hand-held sampling device holster.

6. The apparatus of claim 1 further comprising a global positioning system.

7. The apparatus of claim 1 further comprising a wireless communication transmitter.

8. The apparatus of claim 1 further comprising a wireless communication receiver.

9. The apparatus of claim 1 further comprising a wireless communication transceiver.

10. An apparatus for positively identifying the user of an impairment detection system comprising:
    an alcohol impairment detector with an impairment detector attitude evaluator integral therewith;
    a video camera integral with the impairment detector; and
    a data memory operatively connected to the video camera and adapted to store a plurality of video images.

11. The apparatus of claim 10 wherein the alcohol impairment detector is a breath testing device.

12. The apparatus of claim 10 further comprising an image exposure evaluator operatively connected to the video camera.

13. The apparatus of claim 10 further comprising a hand-held sampling device holster.

14. An apparatus for positively identifying the user of an impairment detection system comprising:
    a means for detecting alcohol impairment with a means for evaluating the attitude of the means for detecting alcohol impairment;
    a means for requesting impairment detection operatively connected to the means for detecting alcohol impairment;
    a means for recording video images integral with the means for detecting alcohol impairment;
    a means for storing data and a plurality of video images operatively connected to the means for recording video images; and
    a means for timing operatively connected to the means for requesting impairment detection and the means for storing data and a plurality of video images whereby selected images corresponding to an impairment detection may be saved.

15. The apparatus of claim 14 wherein the means for requesting impairment detection is a means for visual communication.

16. The apparatus of claim 14 wherein the means for requesting impairment detection is a means for audio communication.

17. The apparatus of claim 14 further comprising a means for evaluating the exposure of an image operatively connected to the means for recording video images.

18. The apparatus of claim 14 further comprising a means for candidly taking surveillance photographs of the occupant of the driver's seat of a motor vehicle.

19. A method for positively identifying the user of an impairment detection system comprising:
    prompting an individual to take an alcohol impairment test;
    evaluating the attitude of an impairment detector;
    recording video images during the alcohol impairment test;
    storing the video images;
    determining whether a proper alcohol detection sample was received;
    determining which video images to save;
    saving a video image corresponding to a specific time during the alcohol impairment test;
    analyzing the sample; and
    providing impairment test feedback to the individual.

20. The method of claim 19 further comprising evaluating the exposure of the video images.

21. A system for monitoring alcohol abstinence of a tester comprising:
    a vehicle;
    a sampling device handpiece adapted to receive a sample located in the vehicle;
    a video camera integral with the handpiece; and
    a test prompter whereby the tester is prompted to provide a sample to the sampling device located in the vehicle.

22. The system of claim 21 wherein the test prompter is a horn.

23. The system of claim 21 wherein the test prompter is a telephone.

24. The system of claim 21 wherein the test prompter is a pager.

25. An apparatus for positively identifying a user, having identifying facial features, of an alcohol impairment detection system comprising:
    a sampling device handpiece adapted to receive a sample; and
    a video camera integral with the handpiece, the camera adapted to capture the identifying facial features of the user and at least part of the handpiece.

26. The apparatus of claim 25 wherein the handpiece has a mouthpiece and the camera is adapted to capture at least part of the mouthpiece.

27. The apparatus of claim 25 further comprising a handpiece holster, the holster positioned and adapted so as to allow the camera to record a panoramic view around the user when the handpiece is positioned in the holster.

28. The apparatus of claim 25 wherein the camera saves a plurality of sequential images.

29. The apparatus of claim 28 wherein the images correspond to predetermined events which occur during use of the alcohol impairment detection system.

30. A system for monitoring alcohol abstinence of a tester having identifying photographic features comprising:
    a parked vehicle;
    a sampling device handpiece adapted to receive a sample located in the vehicle;
    a video camera integral with the handpiece, the camera adapted to capture the photographic features of the tester and at least part of the handpiece; and
    a test prompter whereby the tester is prompted to provide a sample to the handpiece located in the vehicle.

* * * * *

UNITED STATES PATENT AND TRADEMARK OFFICE
CERTIFICATE OF CORRECTION

PATENT NO. : 6,748,792 B1
DATED : June 15, 2004
INVENTOR(S) : Richard C. Freund et al.

It is certified that error appears in the above-identified patent and that said Letters Patent is hereby corrected as shown below:

Title page,
Item [56], References Cited, U.S. PATENT DOCUMENTS, reads "3,824,538....Stemp" and should read -- ...3,824,538....Slemp --.
OTHER PUBLICATIONS, reads "Douglas J. Belmess,..." and should read -- Douglas J. Beirness,... --.

Column 1,
Line 36, reads "install such devises as" and should read -- install such devices as --.

Column 2,
Line 40, 42, 45, reads "the applicant's invention" and should read -- the applicants' invention --.

Column 3,
Line 32, reads "view of showing the use of the" and should read -- view showing the use of the --.

Column 4,
Line 63, reads "such a leaving for working or returning" and should read -- such as leaving for work or returning --.

Column 5,
Line 31, reads "the handheld device" and should read -- the hand-held device --.

Column 6,
Line 12, reads "If the system 10 unitizes a holster 39, the" and should read -- if the system 10 utilizes a holster 39, the --.
Line 55, "duplicate punctuation," should read - received and recorded (Block 54). --.

Column 7,
Line 57, reads "the results of the test, . . .is also saved.", should read -- the results of the test, ...are also saved. --.

UNITED STATES PATENT AND TRADEMARK OFFICE
CERTIFICATE OF CORRECTION

PATENT NO. : 6,748,792 B1
DATED : June 15, 2004
INVENTOR(S) : Richard C. Freund et al.

It is certified that error appears in the above-identified patent and that said Letters Patent is hereby corrected as shown below:

Column 9,
Line 2, reads "begin again.", should read -- begins again. --.
Line 39, reads "not starting or the flashing the lights 27 and", should read -- not starting or the flashing of the lights 27 and --.
Line 41, reads "an early recall for as a result of" should read -- an early recall as a result of --.
Line 48, reads "FIG. 5 Further illustrates", should read -- FIG. 5 further illustrates --.
Line 58, reads "a tester 16, need not necessarily be". should read -- a test 16 need not necessarily be --.
Line 64, reads "intention of the applicant to restrict or, should read -- intention of the applicants to restrict or --.

Column 10,
Line 6, reads "applicant's general inventive concept.", should read -- applicants' general inventive concept. --.

Signed and Sealed this

Thirty-first Day of May, 2005

JON W. DUDAS
*Director of the United States Patent and Trademark Office*